US007820667B2

(12) United States Patent
Ishihara et al.

(10) Patent No.: US 7,820,667 B2
(45) Date of Patent: *Oct. 26, 2010

(54) METHODS OF TREATING HYPERTENSION (75) Inventors: Takafumi Ishihara, Osaka (JP); Yoshiharu Kanayama, Osaka (JP); Mikio Okamura, Osaka (JP); Junichi Yoshikawa, Hyogo-ken (JP); Haruo Shintaku, Osaka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 43 days.

This patent is subject to a terminal disclaimer.

(21) Appl. No.: 11/209,673

(22) Filed: Aug. 24, 2005

(65) Prior Publication Data

US 2006/0009458 A1 Jan. 12, 2006

(51) Int. Cl.
*A61K 31/519* (2006.01)
(52) U.S. Cl. .................................................... 514/250
(58) Field of Classification Search ....................... None
See application file for complete search history.

(56) References Cited

U.S. PATENT DOCUMENTS 5,196,533 A * 3/1993 Ayling et al. ................. 544/118
6,288,067 B1 * 9/2001 Okamura et al. ......... 514/252.16

FOREIGN PATENT DOCUMENTS

| EP | 0722731 | 7/1996 |
| JP | 59-25323 | 2/1984 |
| JP | 59-76086 | 4/1984 |
| JP | 61-277618 | 12/1986 |
| JP | 63-267781 | 11/1988 |
| JP | 7188024 | 7/1995 |
| JP | 07188233 | 7/1995 |
| WO | WO 95/32203 | 5/1995 |
| WO | WO98/08516 | 3/1998 |

OTHER PUBLICATIONS

Cosentio et al., Circulation, 91(1), (1995), 139-144.*
West et al., Journal of Endocrinology, (135, Suppl., p. 62, 1992) (abstract).*
Kukor et al., Placenta, (Jan. 1996), 17(1), pp. 69-73.*
Shintaku et al., Chemistry and Biology of Pteridines and Folates (Jun. 1997), Proceedings of the International Symposium of Pteridines and Folates, pp. 765-769.*
Ishihara et al., Archives of Biochemistry and Biophysics, 298(2), pp. 726-730 (abstract), 1992.*
Sheng et al., J. Neurochem., 61(3), 1120-6 (abstract), 1993.*
Van Amsterdam J.G. and Werner, J. "Tetrahydrobiopterin induces . . . cGMP level" 1992 Eur. J. Pharmacol. vol. 215, pp. 349-350 (abstract).
Fukushima et al., "Analysis of Reduced Forms of Biopterin In Biological Tissues and Fluids", Analytical Biochemistry, 102, 1980, pp. 176-188.

Ujiie et al., "Localization and Regulation of Endothelial NO Synthase mRNA Expression in Rat Kidney", American J. Physiol., 267, 1994, pp. F296-F302.
Hirata et al., "Direct Measurements of Endothelium-Derived Nitric Oxide Release by Stimilation of Endothelin Receptors in Rat Kidney and Its Alteration in Salt-Induced Hypertension", Circulation, vol. 91, No. 4, 1995, pp. 1229-1235.
Hayakawa et al., "Long-term Administration of L-Arginine Improves Nitric Oxide Release From Kidney in Deoxycorticosterone Acetate-Salt Hypertensive Rats", Hypertension. vol. 23, No. 6, Part 1, 1994, pp. 752-756.
Rector et al., "Randomized, Double-Blind, Placebo-Controlled Study of Supplemental Oral L-Arginine in Patients With Heart Failure", Circulation, vol. 93, No. 12, 1996, pp. 2135-2141.
Egashira et al., "Effects of L-Arginine Supplementation on Endothelium-Dependent Coronary Vasodilation in Patients With Angina Pectoris and Normal Coronary Arteriograms", Circulation, vol. 94, No. 2, 1996, pp. 130-134.
Ishihara et al. Archives of Biochemisty and Biophysics, 298(2), pp. 726-730 (abstract).
Sheng et al., J. Neurochem., 61(3), 1120-6 (abstract).
Biochemical and Biophysical Research Communications, vol. 215, No. 3, pp. 1119-1129, (1995); Pei-Feng Chen et al. "Cysteine 99 of Endothelial Nitric Oxide Synthase (Nos-III) is Critical For Tetrahydrobiopterin-Dependent Nos-III Stability and Activity".

(Continued)

*Primary Examiner*—Phyllis G. Spivack
(74) *Attorney, Agent, or Firm*—Paul E. White, Jr.; Manelli Denison & Selter PLLC (57) ABSTRACT

It is an object of the present invention to provide a therapeutic agent for effectively preventing or ameliorating diseases caused by dysfunction of NOS.

The present invention provides a pharmaceutical composition for preventing and/or treating diseases associated with dysfunction of NOS, comprising as an effective ingredient, a compound of the formula (I):

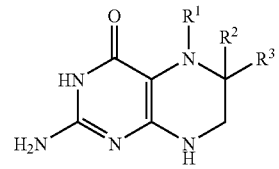

wherein $R^1$ and $R^2$ each represents a hydrogen atom or, taken together with each other, represent a single bond, while $R^3$ represents —CH(OH)CH(OH)CH$_3$, —CH(OCOCH$_3$)CH(OCOCH$_3$)CH$_3$, —CH$_3$, —CH$_2$OH, or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

4 Claims, 7 Drawing Sheets

OTHER PUBLICATIONS

Journal of Cardiovascular Pharmacology, vol. 26, No. 6, pp. 916-922 (1995); Voker Vallon et al. "Interactive Control of Renal Function by a2-Adrenergic System and Nitric Oxide: Role of Angiotensin II".
Science, vol. 272, No. 5262, pp. 689-693, (1996) Gary H. et al. "Molecular Therapies for Vascular Diseases".
Laboratory Investigation, vol. 72, No. 1, pp. 17-24 (1995) Ichiei Narita et al. "Nitric Oxide Mediates Immunologic Injury to Kidney Mesangium In Experimental Glomerulonephritis."
Ann. Med., vol. 27, No. 3, pp. 353-7, (1995) Tikkanen, Iikka et al. "Nitric Oxide in Hypertension and Renal Diseases".
Baker et al. "Plasma From Women With Preeclampsia Increases Endothelial Cell Nitric Oxide Production" Hypertension. 1995, 26, pp. 244-248.
Davidge et al. "NOS expression is increased in endothelial cells exposed to plasma from women with preeclampsia" J. Physiol. Sep. 1995, 268(3 Pt 1):H1 106-12.
Silver et al. "Evaluation of nitric oxide as a mediator of severe preeclampsia" Am. J. Obste. Gynecol. Oct. 1996, 175(4 Pt 1):1013-7.
Scott-Burden, T., "Regulation of Nitric Oxide Production by Tetrahydrobiopterin", Circulation, vol. 91, 1995, pp. 248-250.
Yamamoto et al, "A Comparison of Sepiapterin and Tetrahydrobiopterin Uptake by BRL2H3 Cells," Pteridlnes, vol. 7, 1996, 154-156.
Yaoka et al, "Antihypertensive activity of the angiotensin . . . in various hypertensive animal models," Nippon Yakugaku Zasshi, 1993, 102(1): 35-45 (PubMed abstract only).
Yamamoto et al, "Pharmacological profile of valsartin, . . . effects of valsartan in hypertensive models," Arznelittelforschung, 1997, 47(5): 604-612 (PubMed abstract only).
Nava et al, "Alterations to the nitric oxide pathway in the spontaneously hypertensive rat," J Hypertension, 1998, 16(5): 609-615.
Kulper et al, "Decreased cerebrospinal fluid nitrate levels in Parkinson's Disease, . . . and multiple system atrophy patients," Journal of the Neurological Sciences, 121(1994) 46-49.
Brand et al, "Tetrahydrobiopterin deficiency and brain nitric oxide synthase I the hph1 mouse," J Inherit Metab Dis, 1995, 18(1), 33-39.
Meininger et al., impaired nitric oxide production . . . due to tetrahydrobiopterin deficiency, Biochem J. (2000) 349, 353-356.
Fortepiani and Reckelhoff, "Treatment with tetrahydrobiopterin . . . testosterone synthesis,"Amer. J. Physiol. Regul. Integr. Comp. Physiol. 288:733-736 (2005) (first published Dec. 2004).
Vasques-Vivar et al., "The ratio between tetrahydrobioprterin . . . spin trapping study," Biochem. J. 362: 733-739 (2002).
Channon, K., "Tetrahydrobiopterin, Regulator of Endothelial . . . Vascular Disease," Trends Cardiovasc. Med 14:323-327 (2004).
Kinoshita et al., "Exogenous tetrahydrobiopterin . . . canine basilar artery," Am J Physiol. (Aug. 1996); 271(2 Pt 2): H738-43.
Rosenkranz-Weiss et al., "Regulation of Nitric Oxide . . . Umbilical Vein Endothelial Cells," J. Clin. Invert. 93:2236-2243 (1994).
Van Amsterdam et al., "Tetrahydrobiopterin induces vasodilatation via enhancement of cGMP level," Eur. J. Pharmacol. 215:349-350 (1992).
Lefever et al. 2003 Scientific Sessions of the American Heart Association, Nov. 9-12, 2003, Orlando, Florida, USA: Clinical Pathophysiology of Hypertension, Presentation No. AOP.43.3: 2378,[Published in Circulation, Oct. 28, 2003; 108(17 Suppl):IV1-7870].
Porkert et at., American College of Cardiology ACC.06, Atlanta, Georgia, Mar. 14, Poster Session, Session No. 1027, Presentation No. 1027-194(2006).
BioMarin Pharmaceutical Inc. (Novato, California, Feb. 20, 2007). BioMarin Announces Results from Phase 2 Clinical Study of 6R-BH4 in Poorly Controlled Hypertension. Press Release.

Pinto et al., "Lessons from rat models of hypertension: from Goldblatt to genetic engineering" Cardiovasc Res. Jul. 1988;39(1):77-88.
Mellouk, Sylvie et al. "Nitric Oxide-Mediated Antiplasmodial Activity in Human . . . Exogenous Tetrahydrobiopterin" Infection and Immunity, Sep. 1994, pp. 4043-4046.
Klatt, Peter, et al. "The Pteridine Binding Site of Brain Nitric Oxide Synthase" J. of Biological Chemistry, vol. 269, No. 19, May 13, 1994, pp. 13861-13866.
Kerwin, James et al., "Nitric Oxide: A New Paradigm for Second Messengers" J. Of Medicinal Chemistry, vol. 38, No. 22, Oct. 27, 1995, pp. 4343-4362.
Martasek et al. "Characterization of Bovine Endothelial Nitric Oxide Synthase Expressed in $E.$ $coli$" Biochemical and Biophysical Research Communications, vol. 219, pp. 359-365 (1996).
Schaffner et al. "Tetrahydrobiopterin As Another EDRF In Man" Biochemical and Biophysical Research Communications, vol. 1, pp. 516-523 (1994).
Sonaka et al. "L-Arginine-Nitric Oxide Pathway and Chronic Nephropathy in Aged Rats" vol. 49, No. 4, pp. B157-B161 (1994).
Baker et al., "Plasma From Women With Preeciampsia Increases Endothelial Cell Nitric Oxide Production," Hypertension, V. 26, pp. 244-248 (1995).
Davidge et al., "NOS expression is increased in endothelial cells exposed to plasma from women with preeciampsia." Am J Physiological Soc., V 269, pp. H1106-12 (1995).
Silver et al., "Evaluation of nitric oxide as a mediator of severe preeciampsia," Am J Obstet Gynecol V 175, pp. 1013-17 (1996).
Kojima et al., FEBS, 304(2,3), 163-166 (Jun. 1992).
Hyun et al., Biochem. Biophys. Res. Com., 206(1), 380-386 (Jan. 5, 1995).
Cosentino et al., Circulation, 91(1), 139-144 (Jan. 1995).
Amoah-Apraku et al., J. Am. Soc. Nephrol., 5(8), 1630-31(1995).
Biochemical and Biophysical Research Communications, vol. 215, No. 3, (1995), pp. 1119-1129, Pei-Feng Chen et al. "Cysteine 99 of Endothelial Nitric Oxide Synthase (Nos-III) Is Critical for Tetrahydrobiopterin-Dependent Nos-III Stability and Activity".
Journal of Cardiovascular Pharmacology, vol. 26, No. 6, (1995), pp. 916-922, Volker Vallon et al., "Interactive Control of Renal Function by $C_2$-Adrenergic System and Nitric Oxide: Role of Angiotensin II".
Science, vol. 272, No. 5262, (1996), pp. 689-693, Gary H. et al. "Molecular Therapies for Vascular Diseases".
Bune et al., Exp. Nephrol. (4)43-47 (1996).
Kukor et al., Placenta (17), 69-73 (1996).
Tsutsui et al., Circ. Res., 79(2), 336-342 (1996).
Tiefenbacher et al., Circ., 94(6), 1423-29 (Sep. 15, 1996).
Higashi et al., "Effects of L-Arginine Infusion on Renal Hemodynamics in Patients With Mild Essential Hypertension", Hypertension, vol. 25, No. 4, Part 2, 1995, pp. 898-902.
Nava et al., "Basal Production of Nitric Oxide Is Increased, but Inefficacious, in Spontaneous Hypertension", Circulation 92, 1995, pp. I 347.
Gibbons et al., "Molecular Therapies for Vascular Diseases", Science, vol. 272, 1996, pp. 689-693.
Dominiczak et al., "Nitric Oxide and Its Putative Role in Hypertension", Hypertension, vol. 25, No. 6, 1995, pp. 1202-1211.
Sakuma et al., "$N^G$-Methyl-L-Arginine, an Inhibitor of L-Arginine-Derived Nitric Oxide Synthesis, Stimulates Renal Sympathetic Nerve Activity In Vivo", Circulation Research, vol. 70, No. 3, 1992, pp. 607-611.
Science, vol. 272, No. 5262, pp. 689-693, (1996) Gary H. et al. "Molecular Therapies for Vascular Diseases".

* cited by examiner

METHODS OF TREATING HYPERTENSION

FIELD OF THE INVENTION

The present invention relates to a pharmaceutical composition for preventing and/or treating diseases associated with dysfunction of NOS, comprising as an effective ingredient, a compound of the formula (I):

wherein $R^1$ and $R^2$ each represents a hydrogen atom or, taken together with each other, represent a single bond, while $R^3$ represents —CH(OH)CH(OH)CH$_3$, —CH(OCOCH$_3$)CH(OCOCH$_3$)CH$_3$, —CH$_3$, —CH$_2$OH, or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

PRIOR ART

Vascular endothelium has been known to play an important role in vascular tonus or thrombopoiesis, and it was in 1980 that the presence of endothelium-derived relaxing factor (EDRF) was first reported. The entity of EDRF was proved to be nitrogen monoxide (NO) in 1987. NO is produced when L-arginine is oxidized from $N^G$-hydroxyl-L-arginine into L-citrulline and the reaction is catalyzed by an enzyme named NO synthase (NOS). NOS widely exists in vascular endothelium, nervous systems, kidneys, platelets, cardiac muscles, smooth muscles, etc. and has an important role in control of systemic circulation because the resultant NO has a wide variety of actions. The following diseases with decreased NO production are known: cardiovascular diseases such as hypertension, hyperlipemia, arteriosclerosis, ischemic heart disease, heart failure, thrombosis; respiratory diseases such as asthma, chronic obstructive pulmonary diseases, pulmonary hypertension, ARDS; gastrointestinal diseases such as hepatopathy, liver cirrhosis, gastrointestinal mucosa disorder, hypertrophic pyloric stenosis, pancreatitis; cerebrovascular diseases such as cerebral ischemia, infarction, cerebrovascular failure, senile dementia; renal or urologic diseases such as renal disorder, impotence; gynecological diseases such as toxemia; infectious diseases, immunological disorders, diabetes, burns; or diseases caused by drugs which decrease NO production. The gene for NOS was cloned and structurally analyzed. As a result, the gene for NOS was found to contain a binding site for (6R)-L-erythro-5,6,7,8-tetrahydrobiopterin (hereinafter referred to as "BH4") included in compounds of the formula (I) as active ingredients of the present invention, in addition to those for coenzymes such as calmodulin (CaM), flavin, NADPH. Moreover, BH4 has been suggested to actually be involved in control of the function of NOS.

On the other hand, it was reported that blood pressure rose in experimental animals which had been intravenously injected with an NOS inhibitor (Sakuma I. et al., Circ. Res. 70: 607-611, 1992). Decreased production of endogenous NO was also reported in animal model of hypertension such as DOCA-salt hypertension rats, SHR-SP rats, Dahl-S rats, Goldblatt hypertension rats.

However, the cause for decreased NO production in these models has not been cleared. There are also a number of reports that NO production is rather enhanced in spontaneous hypertension rats (SHR) which are often used as hypertensive model animals (Dominizak AF et al., Hypertension 25: 1202-1211, 1995). In case of SHR, it may also be assumed that NO is excessively released against hypertensive condition to lower blood pressure but the action of NO is insufficient (Nava E. et al., Circulation 92: I-347, 1995). Although it has been pointed out that NO may be implicated in the etiology of hypertension, the relationship between the activity of NOS and hypertension has not been fully elucidated yet. The decrease of vasodilative reaction in hypertension may also be caused by the decreased activity of the endothelium-derived hyperdepolarization factor (EDHF) or an increase in the amounts of the endothelium-derived circulating factor (EDCF), both of which have been unknown about their entity.

Thus, the vasorelaxing action of NO and control of NOS functions by BH4 have been known to some degree. However, the cause for decreased NO production and the relationship between NOS activity and hypertension have not been elucidated, and nothing has been known about antihypertensive action of BH4, as well as the role of BH4 in blood pressure regulation.

In many industrialized countries, cardiovascular diseases are one of the main causes of death. Various drugs such as antihypertensives, antihyperlipemic agents, diuretics, vasodilators, antiplatelets have been used in the treatment of diseases. However, many of them are designed to improve parameters such as blood pressure or cholesterol level, but still unsatisfactory in the prevention of occurrence, retardation of deterioration or progress and long-term prognosis of these diseases. Recently, on the above-mentioned diseases, by investigating at a molecular level, a therapeutic strategy directed to blood vessels especially endothelial cells has been proposed and as one of the most promising therapies, treatment with an agent which regulates the production of the entity of EDRF, i.e. NO, or an agent which has an antioxidant action has been presented. (Gibbons, G. H., Dzau, V. J., Science. Vol. 272, 689-693, 1996). However, any drug or therapy that satisfies this therapeutic strategy has not been established yet.

Nitrate agents (nitroglycerin preparations, etc.) have been considered to be effective as exogenous NO donors for treating angina, heart failure or the like among the above diseases, but they show tolerance over long-term use. Namely, thiol groups (SH groups) become depleted during long-term use of nitrate agents, because SH groups are indispensable for NO production from these nitrate agents. Moreover, the balance of other endogenous substances may be disturbed during long-term use, because NO production requires metabolic enzymes and other NO-related materials such as nitrosothiol are produced during the reaction. A new type of NO donors with the properties of β-blockers or K$^+$ channel openers have also been developed, but they are still within the range of the above-mentioned NO donors. Therefore, improvement of the functions of endothelial cells through regulating endogenous NO function is proposed to be one of the most ideal therapeutic ways for the prevention of occurrence, retardation of deterioration or progress and long-term prognosis of these diseases.

Spontaneous NO production in vivo or activation of NOS seems to be the best therapeutic method. A substrate for NOS, L-arginine, has been examined for its effects against such diseases as hypertension (Higashi, Y. et al., Hypertension 1995, 25, 898-902), angina (Egashira, K. et al., Circulation 1996, 94, 130-134), heart failure (Rector T. S. et al., Circulation 1996, 93, 2135-2141) or the like.

However, it was reported that endothelium-dependent vasodilatation reaction and renal NO production were recovered only partially by long-term administration of L-arginine (Hayakawa H., Hirata Y., Omata M. et al., Hypertension 1994; 23: 752-756) in DOCA salt hypertension rats, a well known hypertensive model in which endothelium-dependent vasodilatation reaction by acetylcholine and renal NO production at basal and by the stimulation of endothelin receptors ($ET_B$) are decreased (Hirata Y., Hayakawa H., Omata M. et al., Circulation 1995: 91: 1229-1235). It was also reported that L-arginine administration resulted in a decrease of blood pressure in hypertension patients similarly to healthy people, but did not bring about an increase in renal bloodflow and the decrease in filtration fractionation and resistance of renal vessels as found in healthy people, and significant decrease in cGMP in blood was observed in hypertension patients (Higashi Y., Ohshima T., Kajiyama G. et al., Hypertension 1996: 25: 898-902). These facts suggest that insufficient NO production in renal circulation may neither result from the lack of the substrate L-arginine nor from only the decline of the enzymatic activity of NOS. Accordingly, the participation of L-arginine-NO system in control of renal circulation and the mechanism of decline of endothelium-dependent vasodilatation reaction can not be explained by insufficient utilization or lack of the substrate L-arginine. Therefore, whether the change of the NOS activity or quantity is involved in these phenomenon should be further investigated.

The purpose of antihypertensive therapy is to prolong the life of patients in a satisfactory condition by preventing cardiovascular complications due to hypertension. For this purpose, blood pressure must be controlled for a long period over life span by antihypertensives in addition to the general therapies such as salt reduction, amelioration of obesity kinesitherapy etc.:

Major antihypertensives therapeutically used at present include thiazides, β-blockers, Ca-antagonists, angiotensin converting enzyme (ACE) inhibitors and $α_1$-blockers. However, none of them satisfy all the following conditions desirable for antihypertensives:

1. Mild action and stable effects;
2. Less side effects at an early stage of use;
3. Desirable influence on circulatory systems and organic functions;
4. No undesirable effects on factors detrimental to cardiovascular systems but rather improvement over long-term use;
5. Better compliance of patients with therapy;
6. No contraindication due to various complications and accidental symptoms;
7. More satisfactory life can be expected as a result of therapy.

Currently used antihypertensives have the following problems.

Thiazide-based diuretics are favorably applied when salt limitation is difficult to obey or a tendency of fluid retention is observed, but are not be recommended to patients with abnormal glucose tolerance, hyperuricemia, renal dysfunction, hyperlipemia or hypokalemia.

β-blockers are favorably applied for young or tachycardiac patients, but are not recommended to patients with bronchial asthma, chronic obstructive pulmonary diseases, obstructive lesions in peripheral arteries or Raynaud's symptoms. They are also inappropriate for hypertension patients with diabetes because of the influence on insulin secretion.

Dihydropyridine derivatives among Ca antagonists have the following side effects, i.e. their vasodilating action may produce facial flush and headache, and their strong hypotensive action may cause hypotension, vertigo and tachycardia or palpitation due to reflex hypersympathicotonus.

ACE inhibitors have side effects such as orthostatic hypotension, dry cough, vascular edema, hyperkalemia etc. In cases of renal dysfunction, attention should be paid to the dosage and hyperkalemia because they are mainly excreted from kidney. Some of them have been reported to give harmful effects on fetus, and therefore contraindicated for pregnant women.

$α_1$-blockers should be carefully applied so as not to cause side effects such as orthostatic hypotension.

Thus, no drug is completely satisfactory in terms of side effects, safety during long-term use and improvement in QOL at present, though many antihypertensive agents with various actions exist. In addition, the primary object of antihypertensive therapy consists in preventing the progress of hypertension-induced organic disorders and lowering the incidence of heart failure, renal failure or cerebral apoplexy and the mortality therefrom. Antihypertensive therapy can not prevent an increase in the number of patients with hypertension-induced renal failure, although it was reported that antihypertensive therapy improved the mortality of heart failure and cerebral apoplexy. In acute or chronic glomerulonephritis or the like, hypertension is produced by glomerular disorder. It has been shown that chronic glomerulonephritis with hypertension has a bad prognosis, and hypertension is one of independent prognostic exacerbation factors in chronic glomerulonephritis. However, no therapy for the hypertension with chronic glomerulonephritis has been established.

Therefore, therapeutic agents providing truly desirable actions are required, and especially the development of agents having a renal protective action are highly demanded.

The compounds of the formula (I) as effective ingredient(s) in the therapeutic agents of the present invention, are known compounds for use in therapeutic agents against malignant hyperphenylalaninemia, depression, Parkinson's disease, etc. For example, refer to Japanese Patent Public Disclosure (KOKAI) Nos. 25323/84, 76086/84, 277618/86 and 267781/88.

SUMMARY OF THE INVENTION

The object of the present invention is to provide a safe therapeutic agent for diseases associated with dysfunction of NOS which improves circulating and organic functions, retards the progress of complications and improves the quality of life of patients by preventing the decrease of endogenous NO production and regulating the functions of endothelial cells.

Based on the results of various studies, it is hypothesized that BH4 level might also be lowered in diseases associated with dysfunction of NOS. Thus, BH4 was administered to DOCA-salt hypertension rats and DOCA-salt SHRs to test the hypothesis. BH4 level and more surprisingly, NOS expression level were found to be actually lowered in the DOCA-salt hypertension rats. In BH4 administration, decrease of endogenous NO production was prevented and physiologically natural antihypertensive effects were obtained. DOCA-salt SHRs also actually exhibited a decline of BH4 level as well as histopathological findings such as necrotizing glomerulitis and necrotizing angiitis, In BH4 administration, antihypertensive effects as well as remarkable improvement effects on said histopathological findings by regulating the functions of endothelial cells were obtained. Thus, the present invention was accomplished on the basis of the finding that BH4 has an action to activate the decreased function of NOS. Accordingly, the present invention is directed to effective therapy with BH4 preparations for diseases associated with dysfunction of NOS.

DETAILED DESCRIPTION OF THE INVENTION

The present invention relates to a pharmaceutical composition for preventing and/or treating diseases associated with dysfunction of NOS, comprising as an effective ingredient, a compound of the formula (I):

wherein $R^1$ and $R^2$ each represents a hydrogen atom or, taken together with each other, represent a single bond, while $R^3$ represents —CH(OH)CH(OH)CH_3, —CH(OCOCH_3)CH(OCOCH_3)CH_3, —CH_3, —CH_2OH, or a phenyl group when $R^1$ and $R^2$ each represents a hydrogen atom, or —COCH(OH)CH_3 when $R^1$ and $R^2$ together represent a single bond, or a pharmaceutically acceptable salt thereof.

As used herein, dysfunction of NOS means that the expression of NOS, which widely occurs in vascular endothelium, nervous systems, kidney, platelets, myocardium, smooth muscles or other organs, has been reduced for some reason or the activity of NOS is not exhibited by dysfunction of these cells even if it is expressed. A typical example of dysfunction of NOS is a decrease in the endogenous NO level. Diseases associated with dysfunction of NOS include those induced, deteriorated or hindered from cure by dysfunction of NOS, such as hypertension, hyperlipemia, arteriosclerosis, coronary vasospasm, ischemic heart disease, heart failure, thrombosis, pulmonary hypertension, cerebrovascular failure, cerebral vasospasm, glomerulonephritis, chronic renal failure, diabetes, postoperative restenosis, achalasia, portal hypertension, hepatic disorder, gastrointestinal mucosa disorder, hypertrophic pyloric stenosis, enteritis, impotence, chorioretinopathy, etc.

When administered to patients with these diseases, BH4 can prevent or treat these diseases by normalizing the functions of NOS through the stimulating effect on NOS production in vivo or through restoring the decreased function of endothelial cells.

Accordingly, the present invention is applied to treat or prevent diseases that can be treated by the stimulatory action of BH4 to activate the function of NOS.

Compounds of the formula (I) as effective ingredients of the present invention include the following ones and pharmaceutically acceptable salts thereof:

(6R)-L-erythro-5,6,7,8-tetrahydrobiopterin (BH4)

(6R,S)-5,6,7,8-tetrahydrobiopterin,
1',2'-diacetyl-5,6,7,8-tetrahydrobiopterin sepiapterin

6-methyl-5,6,7,8-tetrahydropterin 6-hydroxymethyl-5,6,7,8-tetrahydropterin 6-phenyl-5,6,7,8-tetrahydropterin Among the above compounds, 5,6,7,8-tetrahydrobiopterins or salts thereof are preferable, and BH4 or salts thereof are the most preferable.

Compounds of the formula (I) used as effective ingredients in the present invention are known compounds. For example, refer to Japanese Patent Public Disclosure (KOKAI) Nos. 25323/84, 76086/84, 277618/86 and 267781/88. These compounds may be used as appropriate salts with pharmacologically non-toxic acids, including mineral acids such as hydrochloric acid, phosphoric acid, sulfuric acid, boric acid; and organic acids such as acetic acid, formic acid, maleic acid, fumaric acid, mesylic acid.

A pharmaceutical composition of the present invention is effective against the above mentioned diseases. For example, it is effective against hypertension including not only essential hypertension but also malignant hypertension with a necrosis of arteriolar walls in the kidney and retina occurring in a short period, and renal hypertension accompanied by renal disorder. Namely, it is effective against all kinds of hypertension such as essential hypertension, renal hypertension, renovascular hypertension, pregnancy-induced hypertension, senile hypertension and adrenal hypertension.

A pharmaceutical composition of the present invention is prepared by formulating a compound of the formula (I) with generally used carriers by conventional procedures into a dosage form suitable for oral, rectal or parenteral administration (including administration into vein and cerebrospinal fluid).

The carrier used for these pharmaceutical formulations generally include excipients, binders, disintegrators, etc. depending on the dosage form chosen.

Typical examples of excipients include starch, lactose, sucrose, glucose, mannitol and cellulose, and examples of binders include polyvinylpyrrolidone, starch, sucrose, hydroxypropyl cellulose, Arabic gum. Examples of disintegrators include starch, agar, gelatin powder, cellulose, CMC, but any other conventional excipients, binders and disintegrators may also be used.

In addition to such carriers, pharmaceutical composition of the present invention may also contain antioxidants for stabilizing effective ingredients. Antioxidants can be appropriately selected from those conventionally used for pharmaceutical preparations, such as ascorbic acid, N-acetylcysteine, L-cysteine, dl-α-tocopherol, natural tocopherol etc. They are used in an amount that stabilizes active ingredient (one or more) and generally, the ratio of an antioxidant between 0.2 and 2.0 parts by weight to 1 part of the active ingredient(s).

Formulations of the present invention suitable for oral administration may be provided in the form of tablets, sublingual tablets, capsules, powders, granules or fine granules, or suspensions in a non-aqueous liquid such as syrups, emulsions or draft (pro re nata preparation) that Contain the prescribed amount of the active ingredient (one or more).

For example, granules are prepared by homogeneously mixing active ingredient (one or more) with one or more auxiliary ingredients such as carriers and antioxidants as mentioned above, followed by granulation and sieving to uniform grain size. Tablets can be prepared by compressing or molding active ingredient (one or more) optionally together with one or more auxiliary ingredients. Capsules are prepared by filling powder or granules of active ingredient (one or more) optionally mixed homogeneously with auxiliary ingredient (one or more) into appropriate capsules using a capsule filling machine or the like. Formulations for rectal administration can be provided as suppositories using conventional carriers such as cacao butter. Parenteral formulations can be provided as dry solids of active ingredient (one or more) sealed in a nitrogen-filled sterilized containers. Such dry solid preparations can be administered to patients after dispersing or dissolving them into a determined amount of sterilized water just prior to administration.

In manufacturing these formulations, antioxidants as mentioned above may preferably added to a mixture of effective ingredient and conventional carriers, and optionally one or more auxiliary ingredients selected from buffers, flavors, surfactants, viscosants, lubricants, etc. can also be added, if needed.

The dosage of active ingredients, i.e. compounds of the formula (I) may vary with the administration route, the symptom to be treated and the patient condition, and the final determination of the dosage should be made by an attendant physician.

For example, an appropriate dosage for treating hypertension ranges from 0.1 to 50 mg/kg (b.w.)/day, and representative optimal dosage is 0.5 to 10 mg/kg (b.w.)/day.

A desired dosage of said active ingredients may be administered once a day or in divided doses of two to four times a day at appropriate interval.

Active ingredients may be administered alone or in combination with pharmaceutical formulations containing other active ingredients suitable for the disease under treatment to facilitate control of the dosage, for example.

In addition to compounds of the formula (I) as effective ingredients, formulations of the present invention may contain at least one auxiliary effective ingredient selected from the substrates or coenzyme or cofactor for NOS such as L-arginine flavins, for example, FAD, FMN, etc., or calcium. More excellent therapeutic effects can be expected when compounds of the formula (I) are mixed with these effective ingredients than when used alone. The proportion of each of said auxiliary effective ingredients in formulations of the present invention is not specifically limited. For example, the weight ratio of at least one selected from L-arginine, flavins and calcium to 1 part of the compounds of the formula (I) may be within the range from 0.1 to 10, preferably 0.5 to 2.

For example, an appropriate dosage of such mixed formulations for treating hypertension ranges from 0.1 to 50 mg/kg (b.w.)/day, preferably 0.5 to 10 mg/kg (b.w.)/day, in terms of the total amount of active ingredients.

A physician may appropriately choose formulations containing compounds of the formula (I) alone or in combination with other active ingredients, depending on the age, condition or other factors of the patient.

The most preferable active ingredients used in the present invention are (6R)-L-erythro-5,6,7,8-tetrahydrobiopterin (BH4) and salts thereof, but (6R,S)-5,6,7,8-tetrahydrobiopterin, 1',2'-diacetyl-5,6,7,8-tetrahydrobiopterin, sepiapterin, 6-methyl-5,6,7,8-tetrahydropterin, 6-hydroxymethyl-5,6,7,8-tetrahydropterin or 6-phenyl-5,6,7,8-tetrahydropterin and salts thereof may also be used. Needless to say, BH4, naturally occurring component is most preferable. BH4 dihydrochloride has little toxicity to rats judging from the fact that an acute toxicity was more than 2 g/kg (b.w.). An optically inactive analogue, (6R,S)-5,6,7,8-tetrahydrobiopterin is also only slightly toxic as reported in Japanese Patent Public Disclosure No. 25323/84 for the treatment of Parkinson's disease, so that it can also be used for the therapy according to the present invention. Other compounds of the formula (I) also show little or no acute toxicity.

The following examples further explain the present invention in detail, but the present invention is not limited to these examples.

EXAMPLES

Example 1

Granules and Fine Granules

To 1 part (by weight) of polyvinylpyrrolldone (Kollidon 30) dissolved in sterilized purified water were added 10 parts of ascorbic acid and 5 parts of L-cysteine hydrochloride to give a homogeneous solution, and then 10 parts of BH4 dihydrochloride were added to prepare a homogeneous solution.

This solution was added to 59 parts of an excipient (mannitol or lactose) and 15 parts of a disintegrant [corn starch or hydroxypropylcellulose (LH-22)], and the mixture was kneaded, granulated, dried, then sieved.

Example 2

Tablets

The homogeneous solution of an active ingredient prepared in Example 1 was mixed with 58 parts of lactose and 15 parts of microcrystalline cellulose, then with 1 part of magnesium stearate and tableted.

Example 3

Capsules

The dosage form prepared in Example 1 filled into capsules, wherein the formulation include 0.2% of magnesium stearate as a lubricant.

Example 4

Injection

| | |
|---|---|
| BH4 dihydrochloride | 1.5 g |
| Ascorbic acid | 1.5 g |
| L-cysteine hydrochloride | 0.5 g |
| Mannitol | 6.5 g |

The above ingredients were dissolved into sterile purified water to make 100 ml and then sterilized, and 1 ml or 2 ml aliquot each was dispensed into a vial or ampule, then lyophilized and sealed.

Example 5

Injection 2.0 g of BH4 dihydrochloride was dissolved in sterile purified water to make 100 ml under an anaerobic atmosphere and then sterilized and sealed in the same way as in Example 4.

Example 6

Suppositories

| | |
|---|---|
| BH4 dihydrochloride | 150 parts |
| Ascorbic acid | 150 parts |
| L-cysteine hydrochloride | 50 parts |

The above ingredients were homogeneously ground and dispersed into 9950 parts of cacao butter.

Example 7

Granules

| | |
|---|---|
| BH4 dihydrochloride | 5 parts |
| Ascorbic acid | 5 parts |
| L-cysteine hydrochloride | 2 parts |

The above ingredients were used to prepare a homogeneous solution.

This solution was added to a homogeneous mixture of 55 parts of mannitol, 1 part of polyvinylpyrrolidone, 14 parts of hydroxypropylcellulose and 5 parts of L-arginine or calcium, and the mixture was kneaded, granulated, dried, then sieved.

Example 8

Granules

| | |
|---|---|
| BH4 dihydrochloride | 5 parts |
| Ascorbic acid | 5 parts |
| L-cysteine hydrochloride | 5 parts |
| Mannitol | 52 parts |
| Polyvinylpyrrolidone (Kollidon 30) | 1 part |
| Hydroxypropylcellulose (LH-22) | 12 parts |
| L-arginine or calcium | 10 parts |

The above ingredients were granulated and sieved in the same way as in Example 7.

Example 9

Granules

| | |
|---|---|
| BH4 dihydrochloride | 5 parts |
| Ascorbic acid | 5 parts |
| L-cysteine hydrochloride | 2 parts |

The above ingredients were used to prepare a homogeneous solution.

This solution was added to a homogeneous mixture of 10 parts of L-arginine or calcium, 50 parts of mannitol, 1 part of polyvinylpyrrolidone (Kollidon 30) and 9 parts of hydroxypropylcellulose (LH-22), and the mixture was kneaded, granulated, dried, then sieved.

Example 10

Preparation of DOCA-salt Hypertension Rats

One kidney was removed from each of 8-week-old Sprague-Dawley rats (supplied from Charles River) except for a control group. Then, the animals were divided into the following three experimental groups.
1). A group given drinking water only (control group); sample size n=3;
2) A group of DOCA-salt hypertension rats prepared by giving 30 mg/kg b.w. of deoxycorticosterone acetate (DOCA) subcutaneously once a week and 1%-saline as drinking water from one week after nephrectomy (DOCA group); n=6;
3) A group of DOCA-salt hypertension rats administered BH4 (10 mg/kg b.w./day) orally (DOCA+BH4 group); n=5.

Urine was collected for 24 hours using a metabolic cage at the start of experiment and after 2, 4 and 5 weeks (at the termination of the observation period). At the termination of the observation period, blood sample was collected from abdominal aorta under anesthesia with Phenobarbital. The kidney was isolated after perfusing with physiological saline, and examined histologically and immunohistologically.

Measurement of Blood Pressure

Blood pressure was measured by the tail-cuff method at the start of experiment and 2, 4 and 5 weeks.

Measurement of $NO_2/NO_3$ in Urine

The measurement was carried out using Nitrate-Nitrite assay kit, (kit No. 780001, Cyman Chemical Company) according to the Griess method. The values of $NO_2/NO_3$ in urine means the activity of NOS, namely, higher the value, higher the activity.

Measurement of BP in Urine

Biopterin (BP), a metabolite of BH4, was measured by a HPLC according to the procedure of Fukushima and Nixon (Anal. Biochem. 102: 176-188, 1980). The effects of BH4 administration are evaluated on the basis of change of BP level in urine.

Immunostaining of Renal Tissue NOS

The expression of endothelial NOS (e-NOS) and brain NOS (b-NOS) in renal tissues was examined in the sections of the isolated frozen renal tissues by immunostaining with anti-e-NOS and anti-b-NOS antibodies (Affinity Bioreagents), respectively.

Measurement of NOS mRNA Expression
a) Extraction of Whole RNA from Renal Tissues Extraction of RNA from renal tissues was performed by the guanidium/cesium chloride extraction method.

Namely, a small amount of tissues collected from renal cortex of the isolated kidney was added immediately to a lysis solution 4M guanidinium thiocyanate and homogenized by a glass/Teflon homogenizer. This lysate was overlaid on 5.7M cesium chloride and centrifuged at 80,000 rpm for 2 hours, then the precipitate was dissolved in 0.1% diethyl pyrocarbonate (DEP) solution. This solution was precipitated with 2.5M ammonium acetate and ethanol at −20° C. for one hour and centrifuged at 10,000 rpm at 4° C. for 20 minutes to give a precipitate. The precipitate was dissolved in 0.1% DEP solution at the concentration of about 1 μg/μl and stored at −20° C. before use.

b) Reverse Transcriptase (RT) Reaction cDNA was synthesized from whole RNA by using MoMLV reverse transcriptase.

In summary, a mixture of whole RNA, primers, buffer and $H_2O$ was heated at 95° C. for 2 minutes and then ice-cooled. Then, the mixture was incubated at 37° C. for 30 minutes to anneal the primers to RNA. Then, a solution containing, 0.2M dithiothreitol (DTT), and 5 mM deoxyribonucleotide (dNTP), RNAasin, and MOMLV reverse transricptase were added to the mixture. The resulted mixture was heated at 90° C. for 5 minutes and the reaction was stopped by ice-cooling.

c) PCR

PCR was performed using cDNA synthesized by the RT reaction as a template.

Specifically, the RT reaction solution was added to a mixture of 5'- and 3'-primers for each of e-NOS to be detected and for malate dehyadrogenase (MDH) used as an internal standard, PCR buffer, 2.5 mM dNTP mixed solution and Taq DNA polymerase. The reaction mixture was overlaid with mineral oil and centrifuged, after which the reaction was started in an automatic PCR apparatus. PCR products were obtained by running 30 cycles wherein each cycle consists of 94° C. for 30 seconds, 50° C. for 30 seconds and 72° C. for 30 seconds. The primers used for the detection of e-NOS and MDH were selected based on the report by Ujiie. K. et al., Am. J. Physiol. 267 (Renal Fluid Electrolyte Physiol. 36): F296-F302. 1994. Specifically, the base sequences of the primers used for the detection of e-NOS were TACGGAG-CAGCAAATCCAC (SEQ ID NO: 1) for 5' primer and CAG-GCTGCAGTCCTTTGATC (SEQ ID NO: 2) for 3' primer. The base sequences of the primers used for the detection of MDH were CAAGAAGCATGGCGTATACAACCC (SEQ ID NO: 3) for 5' primer and TTTCAGCTCAGGGATGGC-CTCG (SEQ ID NO: 4) for 3' primer.

d) Measurement of NOS mRNA Expression by Polyacrylamide Gel electrophoresis and Southern hybridization PCR products were electrophoresed on 5% polyacrylamide gel and NOS mRNA expression was measured by Southern hybridization.

Figure 4:
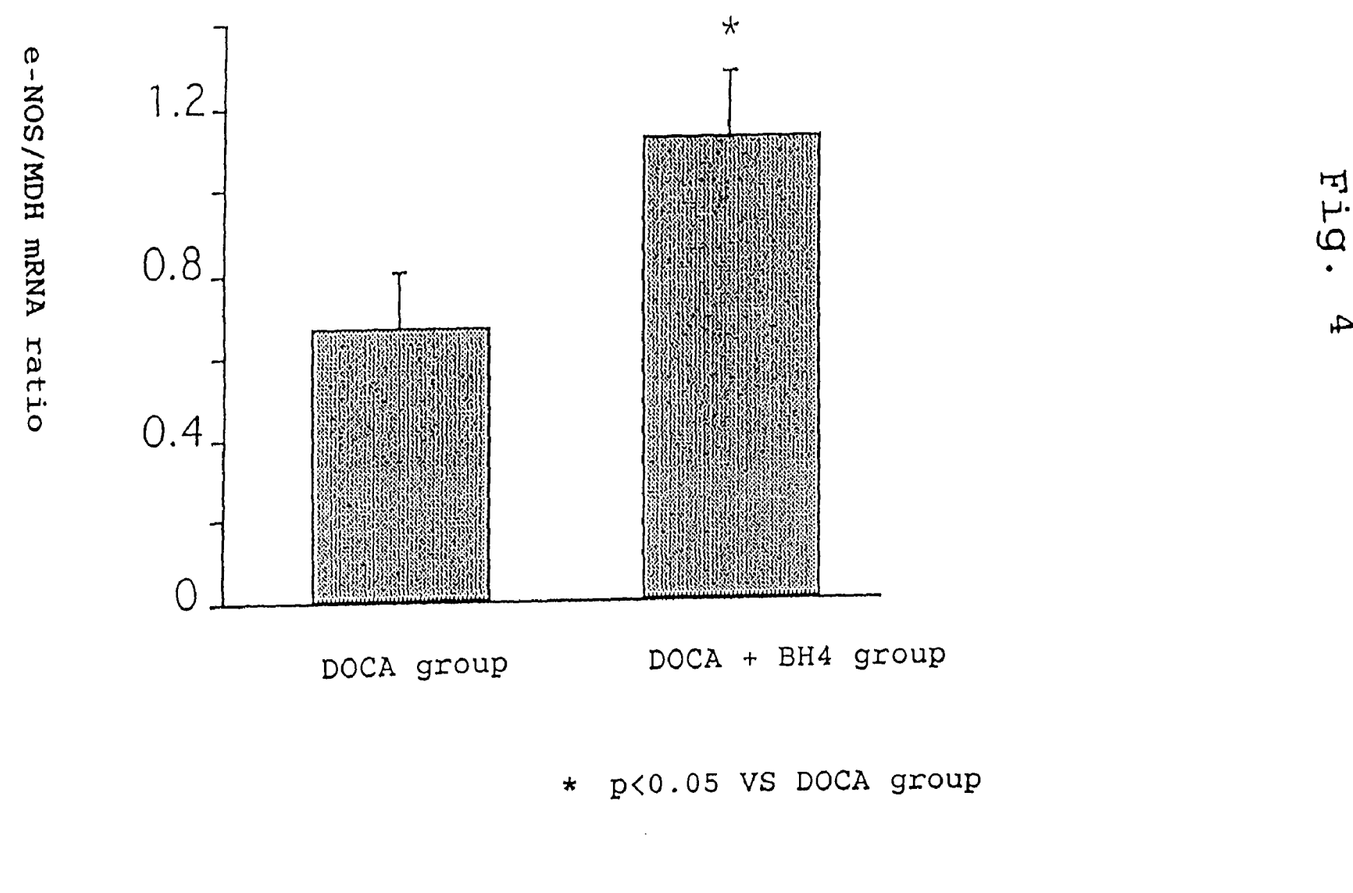
FIG. 4 shows the results of measurement of the expression of E-NOS mRNA in renal tissues.

Specifically, the PCR reaction solution was electrophoresed on 5% polyacrylamide and then, the gel was transferred to membrane filters. Hybridization was performed on the membrane filters using probes labeled with $\gamma^{32}P$-ATP at the 5' prime for the detection of e-NOS and MDH (Ujiie, K. et al., 1994, supra.). The base sequence of the probe was CTGGAA-CAATTTCCATCCG (SEQ ID NO: 5) for the detection of e-NOS and TTTGTCTTCTCCCTGGTGGA (SEQ ID NO:

6) for the detection of MDH. Then, autoradiography was run at −70° C. for several hours and the exposed autoradiograms were analyzed by a densitometer. The results are shown in FIG. 4.

On the basis of the results of autoradiography, the amount of e-NOS PCR products was normalized against the amount of housekeeping gene MDH PCR products to semiquantify e-NOS gene expression.

Statistics

The measured values were expressed as means±standard error and evaluated statistically using to two-way ANOVA test. In the following analyses, the significant level sets $p < 0.05$.

Figure 1:
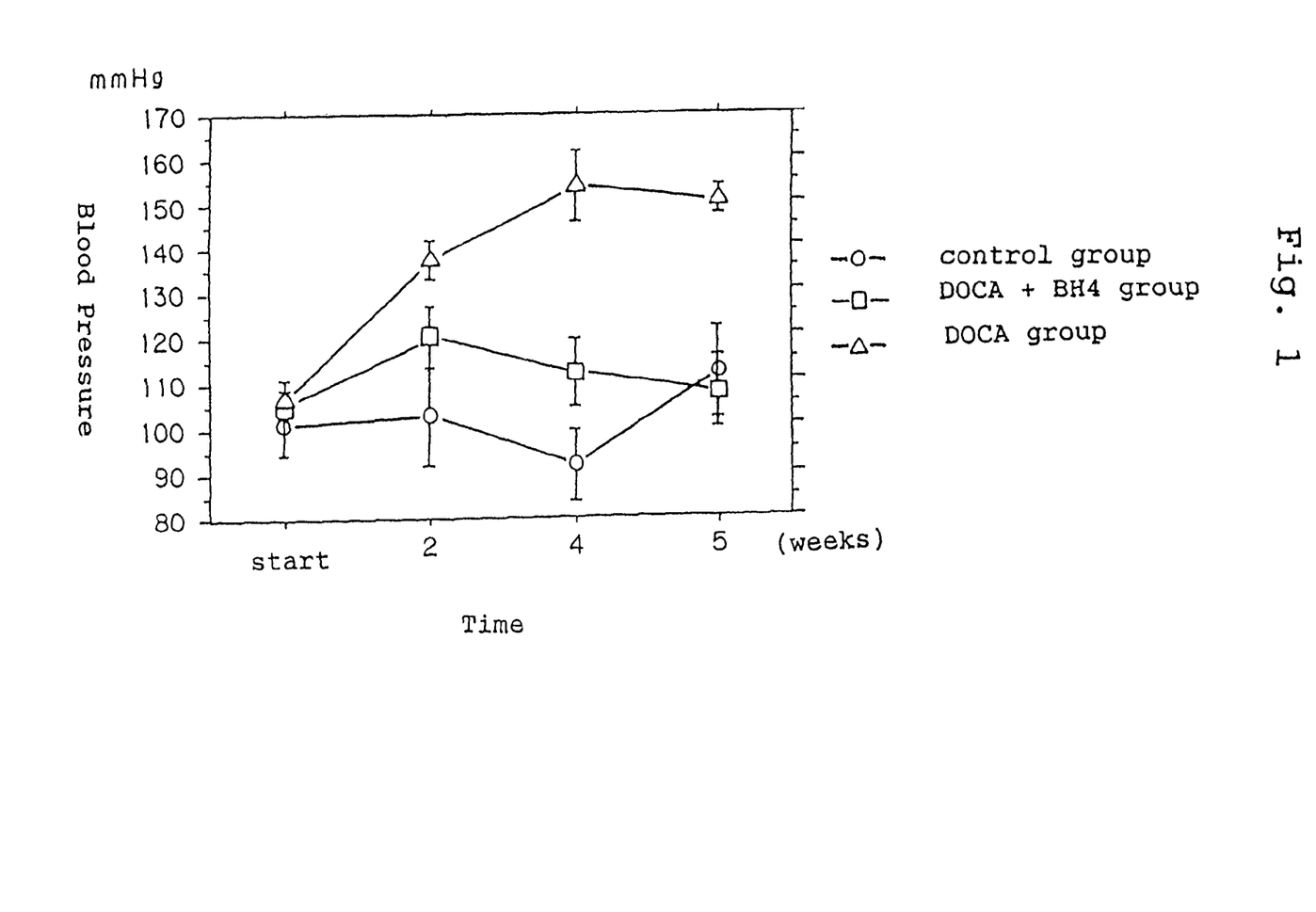
FIG. 1 shows the time course of blood pressure change in a control group (-○-), DOCA group (-Δ-) and a group of DOCA-salt hypertension rats orally administered BH4 (DOCA+BH4 group, -□-).

Change of blood pressure is shown in Table 1 and FIG. 1. DOCA group developed hypertension at week 4 after the start of the observation. The rise in blood pressure in DOCA group was significant as compared with the other two groups. However, DOCA+BH4 group stayed at normal blood pressures similarly to the control group until the termination of the observation period.

TABLE 1

| | Blood pressure (mmHg) | | | |
|---|---|---|---|---|
| | Start | Week 2 | Week 4 | Week 5 |
| Control group | 101.38 (±7.12) | 102.85 (±11.07) | 91.77 (±7.88) | 111.70 (±10.10) |
| DOCA group | 107.03 (±2.04) | 137.53 (±4.63) | 153.53 (±7.71) | 150.68 (±3.35) |
| DOCA + BH4 group | 105.72 (±5.63) | 120.54 (±6.57) | 111.91 (±7.52) | 107.78 (±7.93) |

Figure 2:
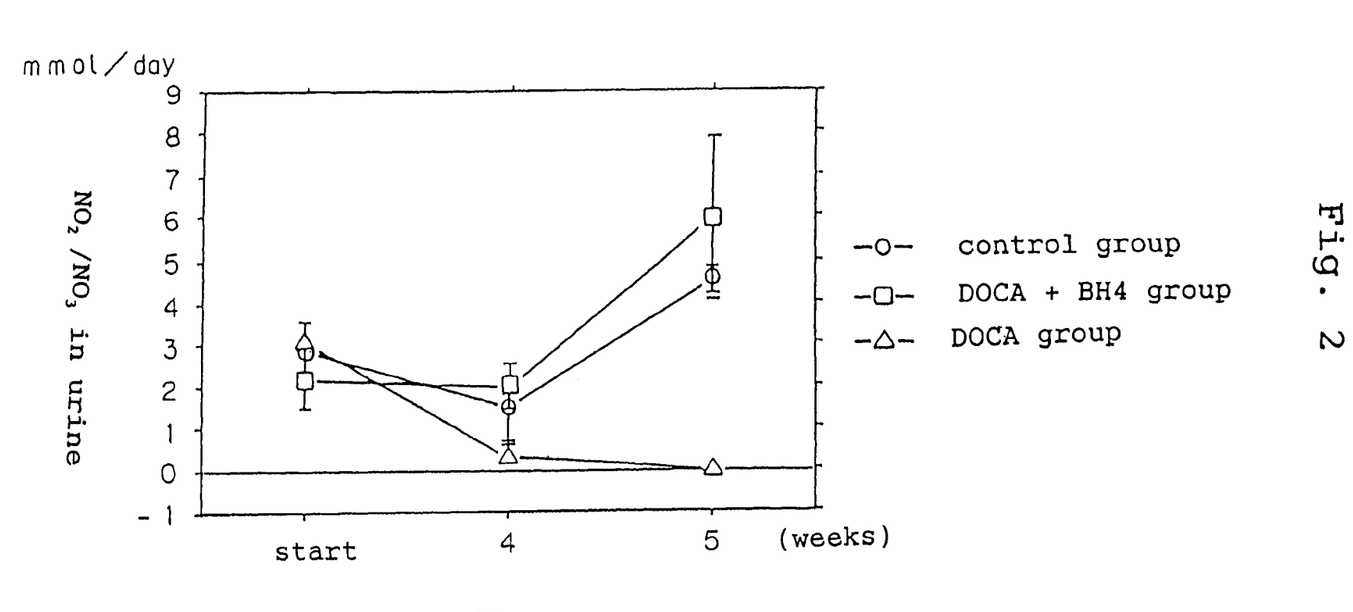
FIG. 2 shows the time course of change of $NO_2/NO_3$ content in urine in a control group (-○-), DOCA group (-Δ-) and a group of DOCA-salt hypertension rats orally administered BH4 (DOCA+BH4 group, -□-).

Change of $NO_2/NO_3$ in urine is shown in Table 2 and FIG. 2. In DOCA group, the value of $NO_2/NO_3$ in urine decreased with time and fell below the measurement sensitivity at the termination of the observation period. However, DOCA+BH4 group showed an increase in the value. The decrease in DOCA group was significant as compared with the other two groups, and no significant difference was found between the control group and DOCA+BH4 group.

TABLE 2

| | $NO_2/NO_3$ in urine (mmol/day) | | | |
|---|---|---|---|---|
| | Start | Week 2 | Week 4 | Week 5 |
| Control group | 2.91 ± 0.09 | | 1.51 ± 0.79 | 4.54 ± 0.32 |
| DOCA group | 3.11 ± 1.09 | | 0.34 ± 0.34 | below detection limit |
| DOCA + BH4 group | 2.22 ± 0.70 | | 2.00 ± 0.55 | 5.95 ± 1.90 |

Figure 3:
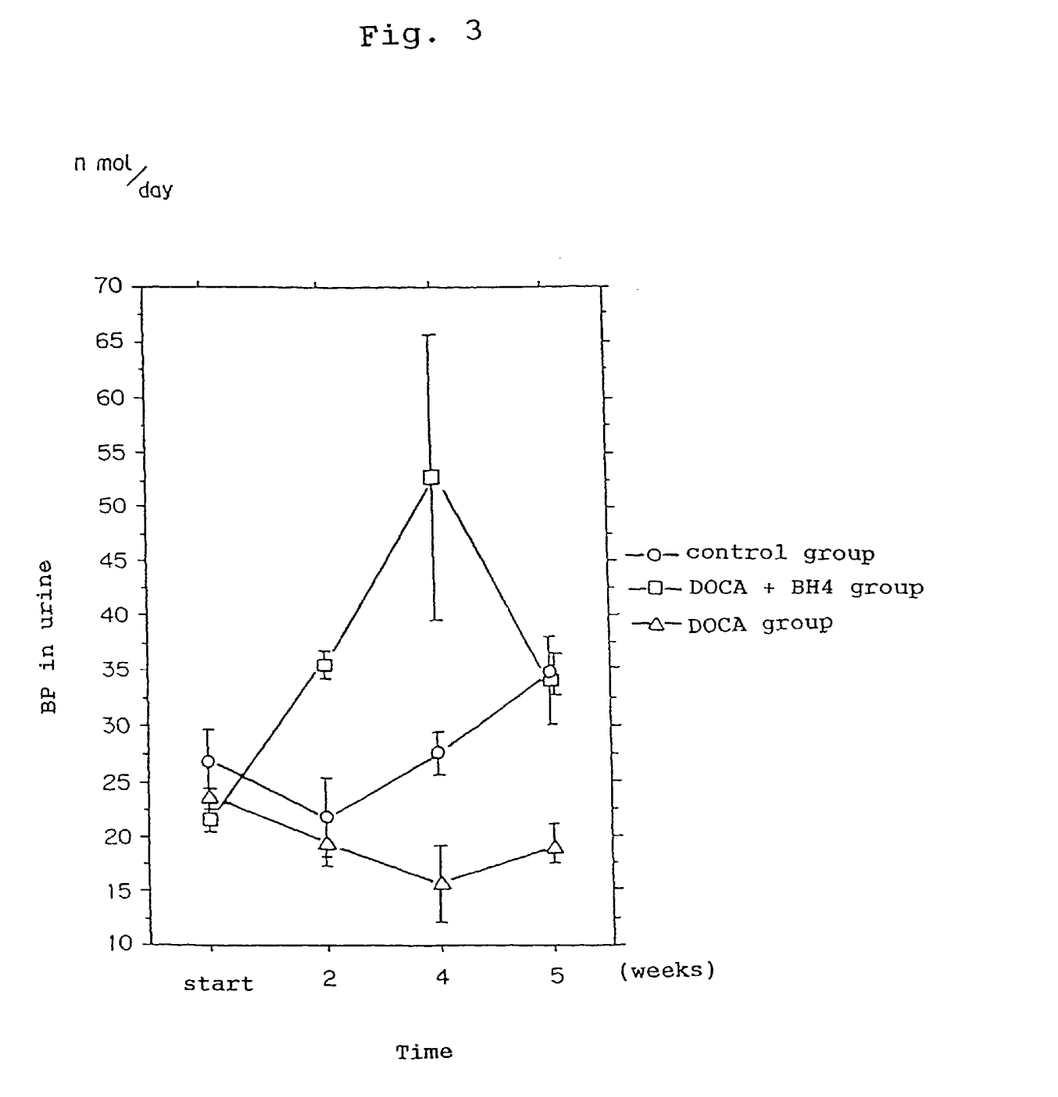
FIG. 3 shows the time course of change of BP content in urine in a control group (-○-), DOCA group (-Δ-) and a group of DOCA-salt hypertension rats orally administered BH4 (DOCA+BH4 group, -□-).

Change of BP in urine is shown in Table 3 and FIG. 3. In DOCA group, the value of BP decreased with time. However, DOCA+BH4 group showed an increase in the value of BP with time. The decrease in DOCA group was significant as compared with the other two groups, and no significant difference was found between the control group and DOCA+ BH4 group.

TABLE 3

| | BP in urine (nmol/day) | | | |
|---|---|---|---|---|
| | Start | Week 2 | Week 4 | Week 5 |
| Control group | 26.76 ± 3.01 | 21.71 ± 0.61 | 27.79 ± 2.03 | 34.96 ± 0.96 |
| DOCA group | 23.77 ± 0.77 | 19.49 ± 2.52 | 15.93 ± 3.46 | 19.25 ± 1.96 |
| DOCA + BH4 group | 21.87 ± 0.60 | 35.58 ± 3.74 | 52.60 ± 13.13 | 34.26 ± 4.08 |

As shown in Table 4, the body weight increased with time in all the groups and no significant difference was found among the three groups.

TABLE 4

| | Body weight (g) | | | |
|---|---|---|---|---|
| | Start | Week 2 | Week 4 | Week 5 |
| Control group | 390.67 ± 18.49 | 433.33 ± 21.49 | 456.00 ± 21.63 | 458.00 ± 20.43 |
| DOCA group | 376.00 ± 3.69 | 399.67 ± 19.44 | 430.33 ± 20.08 | 435.67 ± 23.34 |
| DOCA + BH4 group | 383.40 ± 10.83 | 386.40 ± 12.84 | 431.20 ± 13.31 | 446.80 ± 15.81 |

The results of immunostaining showed that the expression of e-NOS in small vessels and the expression of b-NOS in macula densa both decreased in DOCA group while these expressions in DOCA+BH4 group were comparable to the control group or slightly enhanced.

(Results of Measurement of NOS mRNA Expression)

As shown in FIG. 4, the results of measurement revealed that the expression of e-NOS mRNA was significantly enhanced in DOCA+BH4 group as compared with DOCA group.

As described above, DOCA-salt hypertension rats exhibited a rise in blood pressure, a decrease in $NO_2/NO_3$ in urine and a decrease in NOS expression in renal tissues, indicating that dysfunction of vasoendothelial cells occurred in this model rats. A decrease in BP in urine was also observed in this model rats. On the other hand, oral administration of BH4 suppressed the rise in blood pressure and led to an increase of $NO_2/NO_3$ in urine and an increase of NOS expression in renal tissues, indicating that BH4 is useful for the treatment of diseases caused by decreased endogenous NO production through activating the function of NOS (through regulation of NOS level/NOS activity).

Example 11

Preparation of DOCA-salt SHR

One kidney was removed from 8-week old SHRs (supplied from Charles River) except for a control group. Then, the animals were divided into the following three experimental groups.

1) A group given drinking water only (control group); sample size n=8;
2) A group of DOCA-salt SHRs prepared by giving 30 mg/kg b.w. of deoxycorticosterone acetate (DOCA) subcutaneously once a week and 1% saline as drinking water from one week after nephrectomy (DOCA group); n 4;

3) A group of DOCA-salt SHRs administered BH4 (10 mg/kg b.w./day) orally (DOCA+BH4 group); n=6.

Urine was collected for 24 hours using a metabolic cage at the start of experiment and after 2, 3, 4, 5 and 6 (at the termination of the observation period) weeks. At the termination of the observation period, blood sample was collected from abdominal aorta under anesthesia with Phenobarbital. The kidney was isolated after perfusing with physiological saline, and examined histologically.

Measurement of Blood Pressure

Blood pressure was measured by the tail-cuff method at the start of experiments and after 2, 3, 4, 5 and 6 weeks.

Measurement of BP in Urine

Biopterin (BP), a metabolite of BH4, was measured by a HPLC according to the procedure of Fukushima and Nixon. The effects of BH4 administration are evaluated on the basis of change of BP level in urine.

Histopathological Findings

After collecting urine and measuring blood pressure at 6 weeks, the animals was incised under anesthesia, exsanguinated from abdominal aorta and perfused with physiological saline via this site. The isolated kidney was fixed in a 10% formaldehyde solution, embedded in paraffin, then sliced to 4 μm in thickness by a microtome. Samples were stained with hematoxylin/eosin (HE) and periodic acid-Shiff. The incidences of histopathological findings on necrotizing glomerulitis and necrotizing arteriolitis were compared among the groups.

Statistics

The measured values were expressed as means±standard error and evaluated statistically using two-way ANOVA test. In the following analyses, the significant level sets $p<0.05$.

Figure 5:
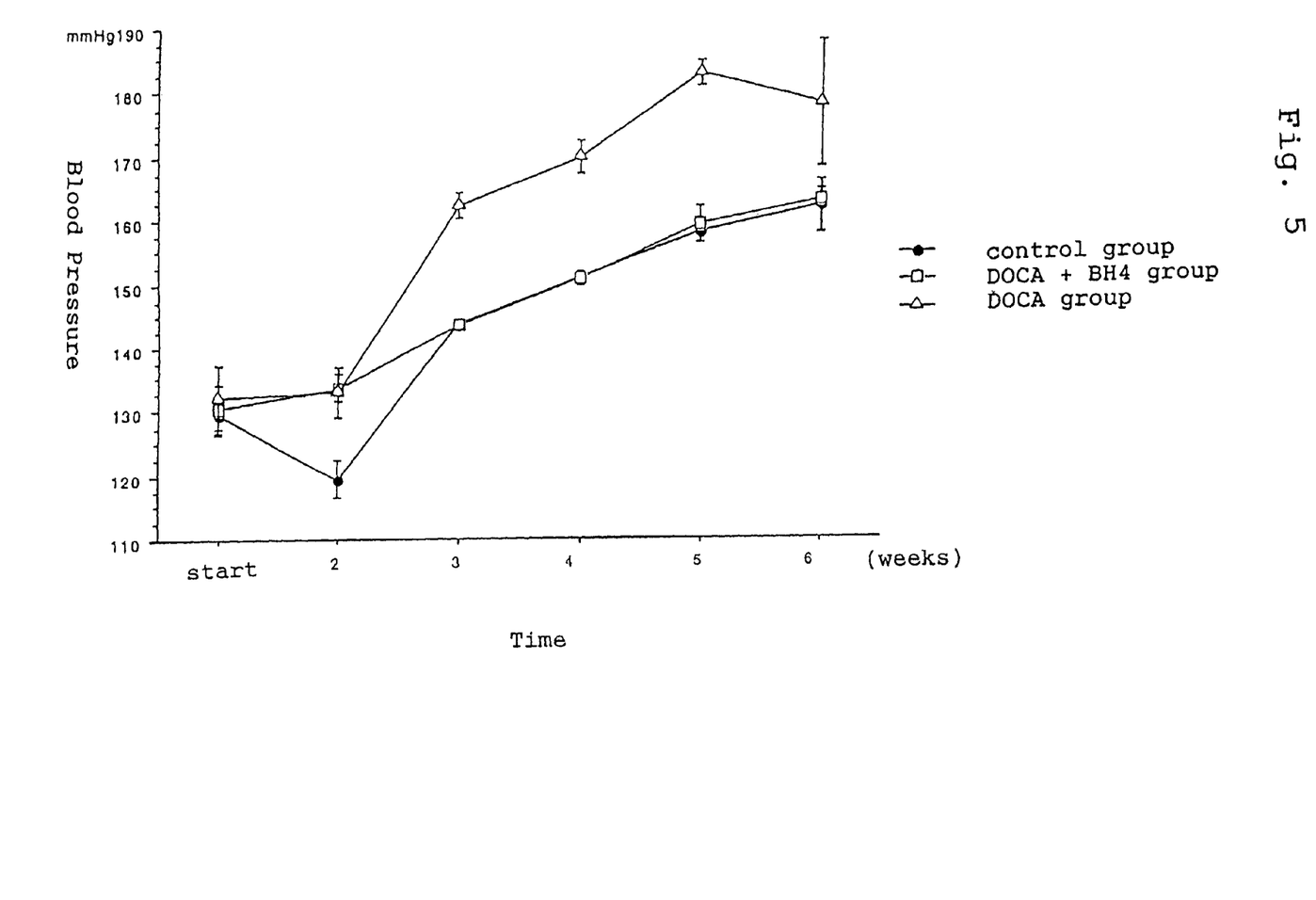
FIG. 5 shows the time course of blood pressure change in a control group (-●-), DOCA group (-Δ-) and a group of DOCA-salt SHRs orally administered BH4 (DOCA+BH4 group, -□-).

Change of blood pressure is shown in Table 5 and FIG. 5. DOCA group developed remarkable hypertension at week 3 after the start of the observation. The rise in blood pressure in DOCA group was significant as compared with the other two groups. However, DOCA+BH4 group showed the same blood pressures level as that of the control group until the termination of the observation period.

TABLE 5

| | Blood pressure (mmHg) | | | | | |
|---|---|---|---|---|---|---|
| | Start | Week 2 | Week 3 | Week 4 | Week 5 | Week 6 |
| Control group | 129.44 (±2.20) | 119.44 (±2.97) | 143.83 (±0.62) | 151.20 (±0.90) | 158.01 (±1.63) | 161.91 (±4.20) |
| DOCA group | 132.00 (±5.18) | 132.88 (±3.88) | 162.28 (±1.87) | 169.83 (±2.57) | 182.98 (±2.04) | 178.10 (±9.85) |
| DOCA + BH4 group | 130.22 (±3.75) | 133.60 (±2.05) | 143.63 (±0.85) | 150.90 (±0.94) | 159.30 (±2.84) | 162.95 (±1.52) |

Figure 6:
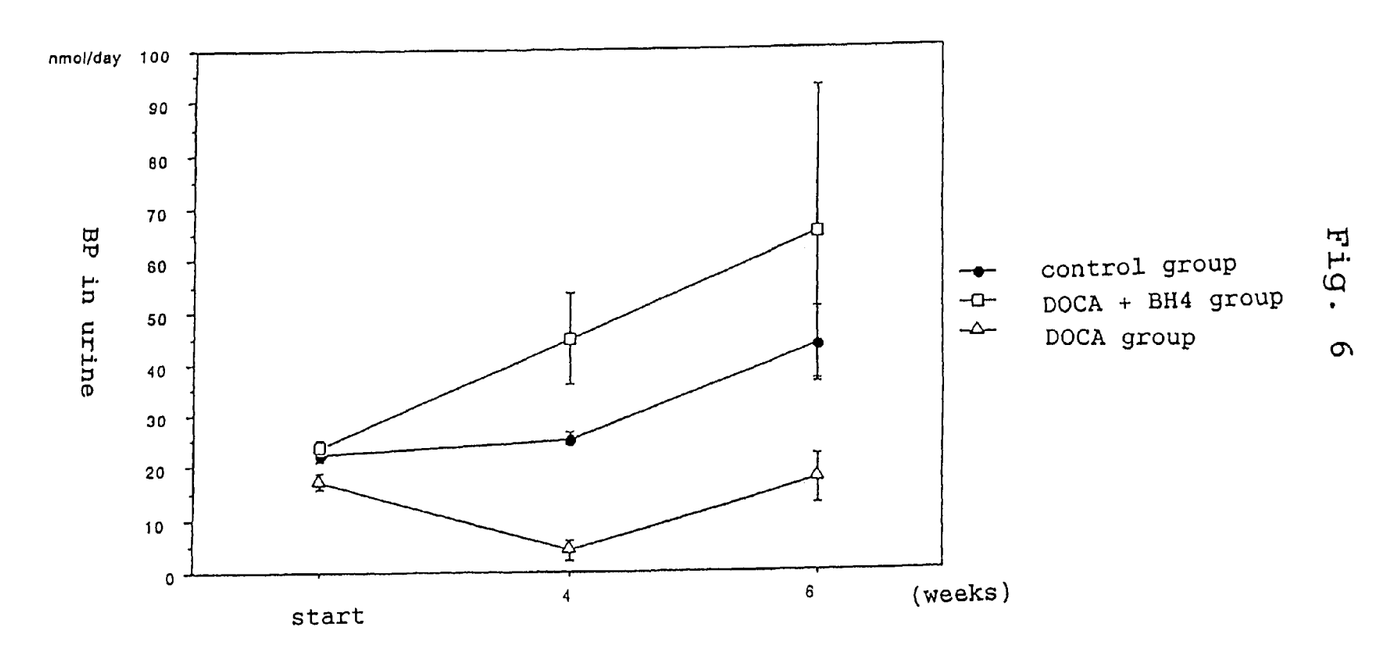
FIG. 6 shows the time course of change of BP content in urine in a control group (-●-), DOCA group (-Δ-) and a group of DOCA-salt SHRs orally administered BH4 (DOCA+BH4 group, -□-).

Change of BP in urine is shown in Table 6 and FIG. 6. In DOCA group, the value of BP decreased with time. However, DOCA+BH4 group showed an increase in the value of BP with time. The decrease in DOCA group was significant as compared with the other two groups, and no significant difference was found between the control group and DOCA+BH4 group.

TABLE 6

| | BP in urine (nmol/day) | | |
|---|---|---|---|
| | Start | Week 4 | Week 6 |
| Control group | 22.29 ± 1.53 | 25.13 ± 1.23 | 43.07 ± 7.24 |
| DOCA group | 17.87 ± 1.65 | 3.18 ± 2.14 | 16.33 ± 5.77 |
| DOCA + BH4 group | 24.26 ± 1.58 | 45.21 ± 10.31 | 71.78 ± 32.08 |

Figure 7:
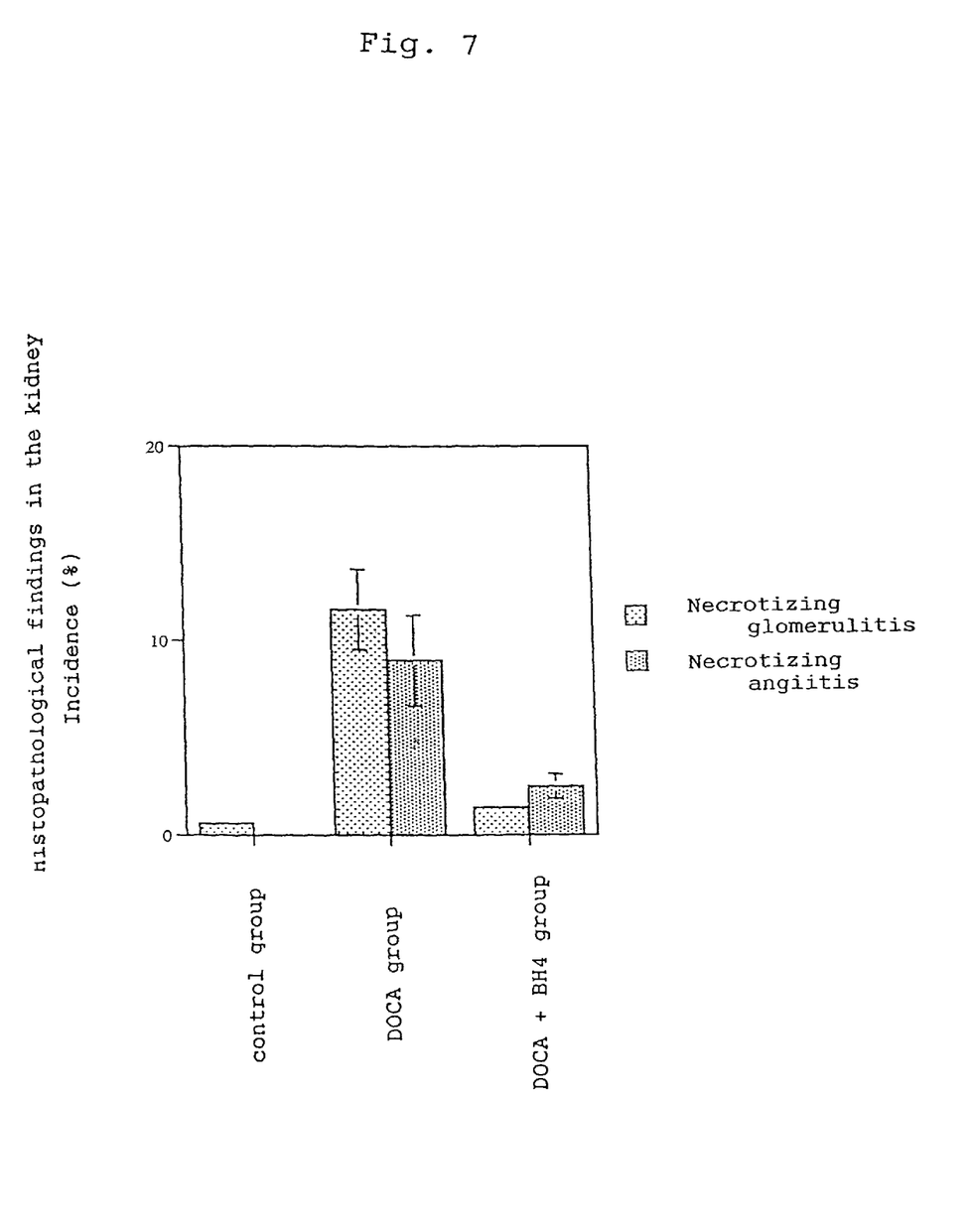
FIG. 7 shows the incidences of histopathological findings in renal tissue samples on necrotizing glomerulitis and necrotizing angiitis in a control group, DOCA group and DOCA+BH4 group.

The incidences of histopathological findings in renal tissue samples are shown in Table 7 and FIG. 7. DOCA group showed significantly higher incidences of necrotizing glomerulitis and necrotizing angiitis as compared with the other two groups.

TABLE 7

| | Percentage (%) of incidences of histopathological findings in renal tissues | |
|---|---|---|
| | Necrotizing glomerulitis | Necrotizing angiitis |
| Control group | 0.06 ± 0.06 | 0.00 ± 0.00 |
| DOCA group | 10.78 ± 0.77 | 9.03 ± 1.65 |
| DOCA + BH4 group | 2.47 ± 1.07 | 3.34 ± 0.94 |

As described above, DOCA-salt SHRs exhibited a rise in blood pressure and histopathological findings of necrotizing glomerulitis or necrotizing angiitis. A decrease in BP in urine was also observed in this model rats. On the other hand, oral administration of BH4 suppressed the rise in blood pressure and remarkably improved histopathological findings, indicating that BH4 is useful for the treatment of diseases associated with dysfunction of endothelial cells through activating the function of NOS.

As has been explained, the present invention provides pharmaceutical composition agents that effectively prevent and/or ameliorate diseases associated with dysfunction of NOS. In addition, active ingredients of therapeutic agents of the present invention have no adverse effects or the like over long-term use because they are substances that inherently exist in vivo.

The invention claimed is:

1. A method of treating hypertension comprising:
administering for at least 4 weeks to a patient in need of such treatment, a therapeutically effective amount of a compound of the formula (I):

wherein $R^1$ and $R^2$ each represents a hydrogen atom, and $R^3$ represents —CH(OH)CH(OH)CH$_3$, or a pharmaceutically acceptable salt thereof, and wherein the compound of formula (I) or a pharmaceutically acceptable salt thereof is administered in a dose range of 0.1 to 50 mg/kg(b.w.)/day.

2. The method of treating hypertension according to claim 1, wherein $R^3$ of the formula I is L-erythro-CH(OH)CH(OH)CH$_3$.

3. The method of treating hypertension according to claim 1 or 2, wherein hypertension is selected from a group consisting of pulmonary hypertension, portal hypertension, essential hypertension, renal hypertension, renovascular hypertension, pregnancy-induced hypertension, senile hypertension and adrenal hypertension.

4. The method of treating hypertension according to claim 1 or 2, wherein the compound of formula (I) or a pharmaceutically acceptable salt thereof is administered in a dose range of 0.5 to 10 mg/kg(b.w.)/day.

* * * * *

UNITED STATES PATENT AND TRADEMARK OFFICE
CERTIFICATE OF CORRECTION

PATENT NO. : 7,820,667 B2
APPLICATION NO. : 11/209673
DATED : October 26, 2010
INVENTOR(S) : Takafumi Ishihara et al.

It is certified that error appears in the above-identified patent and that said Letters Patent is hereby corrected as shown below:

Title page, item (22) should read as follows: (22) PCT Filed: Aug. 29, 1997

Title page, item (86) should read as follows: (86) PCT No. PCT/JP97/03027

§ 371 (c)(1), (2), (4) Date: Jan. 12, 1999

Title page, item (87) should read as follows: (87) PCT Pub. No. WO98/08516

PCT Pub. Date: Mar. 5, 1998

Related U.S. Application Data should read as follows:
item (62) Continuation of application No. 10/408,571, filed on Apr. 8, 2003, which is a Continuation of application No. 09/069,102, filed on Jan. 12, 1999.

Foreign Application Priority Data should read as follows:
item (30)   Aug. 30, 1996   (JP) ...................231103/1996
            Apr. 10, 1997   (JP) ...................92213/1997

Signed and Sealed this
Tenth Day of July, 2012

David J. Kappos
*Director of the United States Patent and Trademark Office*

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Primer used for the detection of e-NOS (as the

```
                                5' primer)

<400> SEQUENCE: 1
tacggagcag caaatccac                                                19

<210> SEQ ID NO 2
<211> LENGTH: 20
<212> TYPE: DNA
<213> ORGANISM: Artificial Sequence
<220> FEATURE:
<223> OTHER INFORMATION: Primer used for the detection of e-NOS (as the
      3' primer)

<400> SEQUENCE: 2
caggctgcag tcctttgatc                                               20

<210> SEQ ID NO 3
<211> LENGTH: 24
<212> TYPE: DNA
<213> ORGANISM: Artificial Sequence
<220> FEATURE:
<223> OTHER INFORMATION: Primer used for the detection of MDH (as the
      5' primer)

<400> SEQUENCE: 3
caagaagcat ggcgtataca accc                                          24

<210> SEQ ID NO 4
<211> LENGTH: 22
<212> TYPE: DNA
<213> ORGANISM: Artificial Sequence
<220> FEATURE:
<223> OTHER INFORMATION: Primer used for the detection of MDH (as the
      3' primer)

<400> SEQUENCE: 4
tttcagctca gggatggcct cg                                            22

<210> SEQ ID NO 5
<211> LENGTH: 19
<212> TYPE: DNA
<213> ORGANISM: Artificial Sequence
<220> FEATURE:
<221> NAME/KEY: iDNA
<222> LOCATION: (1)..(19)
<220> FEATURE: Probe
<223> OTHER INFORMATION: :

<400> SEQUENCE: 5
ctggaacaat ttccatccg                                                19

<210> SEQ ID NO 6
<211> LENGTH: 20
<212> TYPE: DNA
<213> ORGANISM: Artificial Sequence
<220> FEATURE:
<221> NAME/KEY: iDNA
<222> LOCATION: (1)..(19)
<220> FEATURE: Probe
<223> OTHER INFORMATION: :

<400> SEQUENCE: 6
tttgtcttct ccctggtgga                                               20
```